United States Patent
Hourtash

(10) Patent No.: US 8,271,130 B2
(45) Date of Patent: Sep. 18, 2012

(54) MASTER CONTROLLER HAVING REDUNDANT DEGREES OF FREEDOM AND ADDED FORCES TO CREATE INTERNAL MOTION

(75) Inventor: Arjang Hourtash, Santa Clara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 623 days.

(21) Appl. No.: 12/406,004

(22) Filed: Mar. 17, 2009

(65) Prior Publication Data
US 2010/0228266 A1 Sep. 9, 2010

Related U.S. Application Data

(60) Provisional application No. 61/158,708, filed on Mar. 9, 2009.

(51) Int. Cl.
*G06F 19/00* (2011.01)
(52) U.S. Cl. ........... 700/245; 901/8; 901/19; 414/7; 606/130
(58) Field of Classification Search ........... 700/245; 901/8, 19; 606/130; 414/7
See application file for complete search history.

(56) References Cited

U.S. PATENT DOCUMENTS

| | | | |
|---|---|---|---|
| 6,246,200 B1 | 6/2001 | Blumenkranz et al. | |
| 6,364,888 B1 | 4/2002 | Niemeyer et al. | |
| 6,424,885 B1 | 7/2002 | Niemeyer et al. | |
| 6,459,926 B1 | 10/2002 | Nowlin et al. | |
| 6,684,129 B2 | 1/2004 | Salisbury, Jr. et al. | |
| 6,714,839 B2 * | 3/2004 | Salisbury et al. | 700/245 |
| 6,799,065 B1 | 9/2004 | Niemeyer | |
| 7,087,049 B2 | 8/2006 | Nowlin et al. | |

OTHER PUBLICATIONS

J. Yan and S.E Salcudean; Design and Control of a Motion Scaling System for Microsurgery Experiments; Department of Electrical Engineering, University of British Columbia; Vancouver, BC, V6t 1Zf, Canada.

M.W. Thring; Robots and Telechris: Manipulators with Memory; Remote Manipulators; Machine Limbs for the Handicapped; Ellis Horwood Limited; Chichester, West Sussex P019 1EB England; pp. 9-11, 108-131, 194-195, 235-279; 1983.

Jean Vertut and Philippe Coiffet; Teleoperation and Robotics, Evolution and Development; vol. 3A, Robot Technology; English Translation by Prentice-Hall, Inc. 1986.

* cited by examiner

*Primary Examiner* — Thomas Black
*Assistant Examiner* — Luke Huynh

(57) ABSTRACT

An input device includes a handle coupled to a base by a linkage. The handle is manually movable relative to the base to provide a position input. The linkage has a plurality of links including a redundant link that permits internal motion of the linkage such that the linkage can move without moving the handle relative to the base. When a distance between the handle and a handle stop position is less than a threshold distance, a handle stop applies a first load to the handle. A drive system applies a second load to the redundant link responsive to the first load to create internal motion of the linkage that increases a distance between the handle and a handle stop position. The second load may be proportional to a cosine of an angle between a handle axis of motion and a redundant link axis of motion.

24 Claims, 3 Drawing Sheets

MASTER CONTROLLER HAVING REDUNDANT DEGREES OF FREEDOM AND ADDED FORCES TO CREATE INTERNAL MOTION

CROSS REFERENCE TO RELATED APPLICATIONS

This application claims the benefit pursuant to 35 U.S.C. 119(e) of U.S. Provisional Application No. 61/158,708, filed Mar. 9, 2009, which application is specifically incorporated herein, in its entirety, by reference.

BACKGROUND

1. Field

This invention relates to data input devices, and more particularly, to a master controller which may be used for directing movements of a robot and which is particularly useful for robotically enhanced surgery.

2. Background

In robotically assisted surgery, the surgeon typically operates a master controller to remotely control the motion of surgical instruments at the surgical site. The master controller may be separated from the patient by a significant distance (e.g., across the operating room, in a different room, or in a completely different building than the patient). Alternatively, a master controller may be positioned quite near the patient in the operating room. Regardless, the master controller will typically include one or more hand input devices.

These hand input devices are coupled by a servo mechanism to the surgical instrument. More specifically, servo motors move a manipulator or "slave" supporting the surgical instrument based on the surgeon's manipulation of the hand input devices. During an operation, the surgeon may employ, via the robotic surgery system, a variety of surgical instruments such as tissue graspers, needle drivers, electrosurgical cautery probes, etc. Each of these structures performs functions for the surgeon, for example, holding or driving a needle, grasping a blood vessel, or dissecting, cauterizing, or coagulating tissue.

To deliver the full potential of this new form of surgery, the robotic system will preferably allow movement of the surgical end effector in both position and orientation. This requires providing an input device that a surgeon can move freely and with considerable agility. It is desirable that the input device be relatively unconstrained in its range of motion so that only the limitations imposed by the range of motion of the remote surgical tools affect what the surgeon is able to do. Further it is desirable that the input device impose a minimal load on the surgeon's hand to avoid fatigue and to allow precise and delicate movements of the input device.

In light of the above, it would be desirable to provide an improved operator input device for a robotic surgical system that provides a large range of input motions with minimal loading of the operator's hand.

SUMMARY

An input device includes a handle coupled to a base by a linkage. The handle is manually movable relative to the base to provide a position input. The linkage has a plurality of links including a redundant link that permits internal motion of the linkage such that the linkage can move without moving the handle relative to the base. When a distance between the handle and a handle stop position is less than a threshold distance, a handle stop applies a first load to the handle. A drive system applies a second load to the redundant link responsive to the first load to create internal motion of the linkage that increases a distance between the handle and a handle stop position. The second load may be proportional to a cosine of an angle between a handle axis of motion and a redundant link axis of motion.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure the understanding of this description.

Figure 1A:
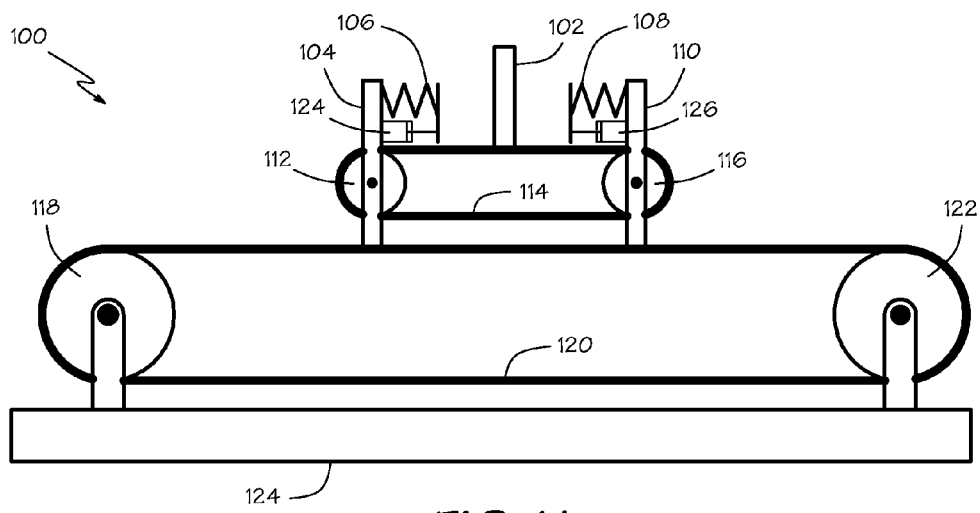
FIG. 1A is a schematic representation of an input device that provides a position input along a single linear axis.

FIG. 1A shows a schematic representation of an input device 100 that provides a linear position input along a single linear axis. A handle 102 is manually movable relative to a base 124 to provide a linear position input. A linkage couples the handle to the base. In the schematic representation of the input device shown, the linkage is in the form of belts on pulleys. The handle 102 is supported by a belt 114 that runs around two pulleys 112, 116. This allows the handle 102 to be manually moved along an axis, right and left as shown in the figure. The handle 102 may be limited in its range of motion such as by the structures 104, 110 that support the pulleys 112, 116. The structures 104, 110 that support the pulleys 112, 116 may be supported in turn by a second belt 120 that runs around a second set of pulleys 118, 122.

It will be appreciated that the second belt 120 provides a redundant link to the base 124 in that it provides no additional freedom of motion for the handle 102. While the second belt 120 is redundant, it may still provide a practical benefit to the input device 100. The first belt 114, which directly supports the input handle 102, may provide a structure for agile and sensitive input motions with a limited range of input. The second belt 120, which supports the structure of the first belt 114, may lack the agility and sensitivity of the first belt structure but provide a broad range of input motion.

Figure 1B:
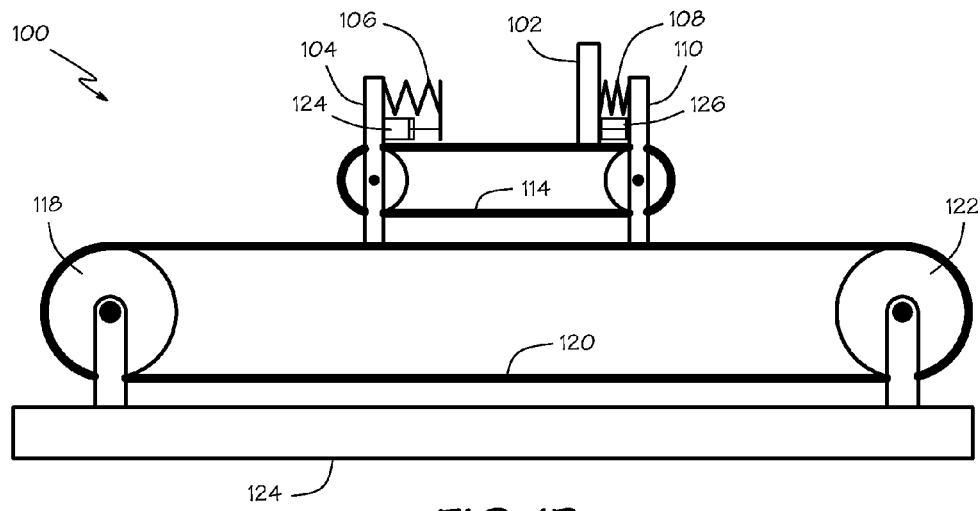
FIG. 1B is a schematic representation of the input device of FIG. 1A in a second configuration.

FIG. 1B shows the input device 100 with the handle 102 having been manually moved to the right, near a handle stop position represented by the pulleys support structure 110. The handle 102 would be unable to be moved further to the right in this configuration of the input device 100.

Figure 1C:
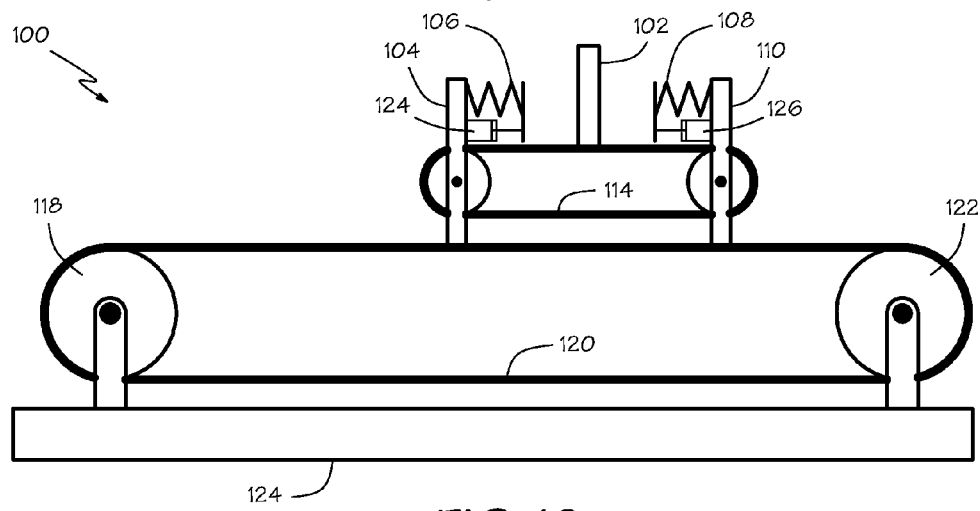
FIG. 1C is a schematic representation of the input device of FIG. 1A in a third configuration.

FIG. 1C shows the input device 100 operating in accordance with an embodiment of the invention. It will be appreciated that the redundant linkage provided by the second belt 120 permits an internal motion of the linkage connecting the handle 102 to the base 124. By "internal motion" it is meant that the linkage can be moved without moving the endpoints, the handle 102 and the base 124, of the linkage.

It will be appreciated that the redundant linkage, such as the second belt 120 and pulleys 118, 122, might accelerate and move at a limited rate either because of the inertia of the redundant linkage or because of limits imposed to avoid movements of the input device 100 that could be distracting to the user. This may make it possible for rapid movements of the input handle 102 to reach the handle stop position 110 before the redundant linkage can restore the range of motion of the handle.

The input device 100 includes a handle stop that applies a first load to the handle 102 when a distance between the handle and a handle stop position 110 is less than a threshold distance. The first load applied by the handle stop pushes the handle 102 away from the handle stop position 110 and may provide a restoring force to move the handle away from the handle stop position if the handle is not being held in position by an operator. In the figure, the load applied by a handle stop is suggested by spring stops 106, 108. As suggested by the springs, the load applied to the handle 102 may increase as the distance between the handle and the handle stop position 110 decreases. Also as suggested by the figure, the load applied to the handle 102 may be applied only when the distance between the handle and the handle stop position is less than a threshold distance. There may be a range of motion in which no load is applied to the handle 102 by the handle stop.

A second load is applied to the redundant linkage of the second belt 120 responsive to the first load applied to the handle. The second load creates an internal motion of the linkage that increases the distance between the handle 102 and the handle stop position 110, thereby reducing the first load applied to the handle if the handle is being held such that the load applied by the handle stop does not move the handle away from the handle stop position. It may be advantageous to use drive systems that apply limited loads to the handle and the redundant link so that the loads applied to the input device can be overcome by the loads manually applied to the input handle 102 by an operator. Accordingly, the second load applied to the redundant linkage may be sufficient to create the internal motion necessary to reduce the load applied to the handle 102 by increasing the distance between the handle and the handle stop position 110 and to overcome the friction in the linkage. A sufficient second load may be proportional to the first load. The second load may be the first load multiplied by a constant to provide the necessary additional load to overcome friction in the linkage.

The handle stop may further include a damping mechanism, such as a dashpot 124, 126, that applies an additional damping load to the handle that is proportional to the velocity of the handle with respect to the handle stop position 110, 112. The damping load increases the first load as the velocity of the handle moving toward the handle stop position increases. Conversely, the damping load decreases the first load as the velocity of the handle moving away from the handle stop position increases. It will be appreciated that a damping load applied to the handle as part of the first load will also damp the load applied to the redundant link since the second load is responsive to the first load.

Figure 2A:
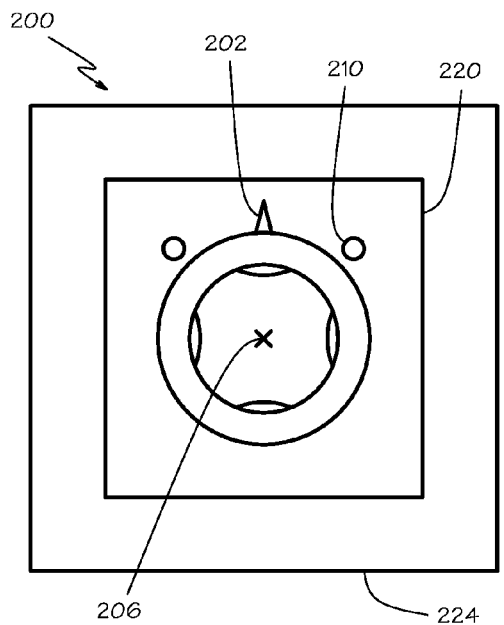
FIG. 2A is a schematic representation of an input device that provides an orientation input about a single axis.

FIG. 2A shows a schematic representation of an input device 200 that provides an angular position input about a single axis 206. A handle 202 is manually rotatable about the axis 206 to provide an angular position input. The handle 202 is coupled to a support 220 by a pivot. The support is coupled in turn to a base 224 by a second pivot. In this input device 200, the support 220 provides a redundant linkage between the handle 202 and the base 224.

Figure 2B:
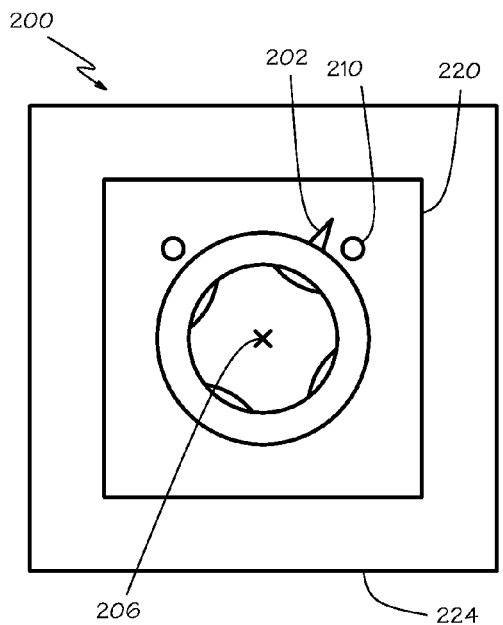
FIG. 2B is a schematic representation of the input device of FIG. 2A in a second configuration.

FIG. 2B shows the input device 200 with the handle 202 having been rotated in a clockwise direction such that the handle is less than a threshold distance away from a handle stop position 210.

Figure 2C:
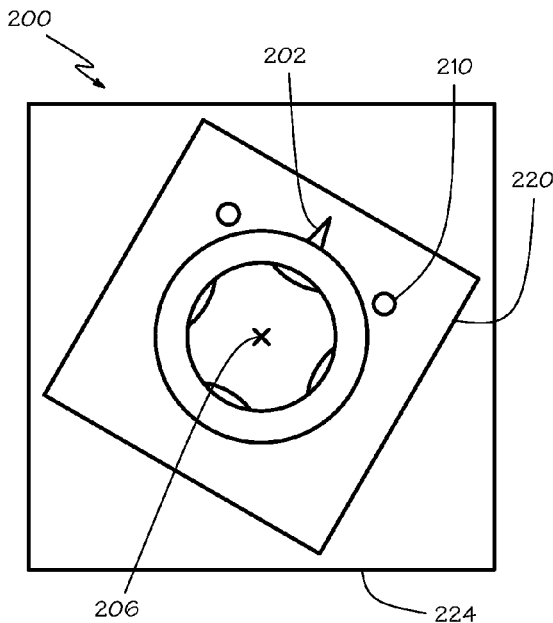
FIG. 2C is a schematic representation of the input device of FIG. 2A in a third configuration.

FIG. 2C shows the input device 200 after a drive system coupled to the redundant link 220 has applied a load to the redundant linkage to cause an internal motion of the linkage that increases the distance between the handle 202 and the handle stop position 210.

Figure 3:
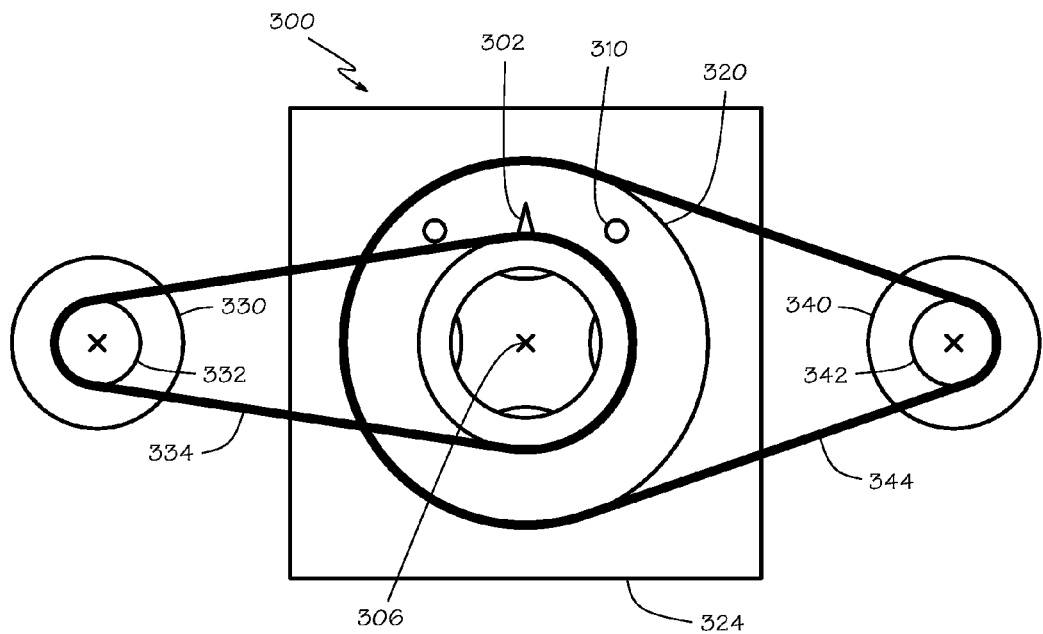
FIG. 3 shows a schematic representation of another input device that provides an orientation input about a single axis.

FIG. 3 shows a schematic representation of another input device 300 that provides an angular position input about a single axis 306. This input device provides a handle 302 that is coupled to a base 324 by a linkage that includes a first pivotal link connecting the handle to a support 320 which is connected by a second pivotal link, which is a redundant link, to a base 324.

The input device 300 includes a handle drive system 330 coupled to the handle 302. The handle drive system 330 may include a motor that turns a pulley 332 to move a belt 334 that rotates the handle 302 about the first pivotal link. The first load applied to the handle 302 by the handle drive system 330 pushes the handle away from the handle stop position 310 and may provide a restoring force to move the handle away from a handle stop position if the handle is not being held in position by an operator. The handle drive system may apply a load to the handle that increases as a distance between the handle and the handle stop position 310 decreases. The handle drive system may further apply a damping load that is added to the first load applied to the handle such that the first load is increased as the velocity of the handle moving toward the handle stop position increases and decreased as the velocity of the handle moving away from the handle stop position increases. By using an active device to provide the load, it is possible to provide characteristics that would be difficult or impossible to provide with a mechanical stop device. For example, the load applied to the handle may increase in a nonlinear fashion. As another example, the handle stop position may not be a fixed position on the support 320; the handle stop position may be determined from the overall configuration of the input device 300.

This input device further includes a linkage drive system 340 coupled to the redundant link provided by the support 320. The linkage drive system 340 may include a motor that turns a pulley 342 to move a belt 344 that rotates the support 320 about the second pivotal link. The linkage drive system 340 applies a second load to the redundant link responsive to the first load to create internal motion that increases the distance between the handle and a handle stop position 310 in a similar manner to that described above.

Figure 4:
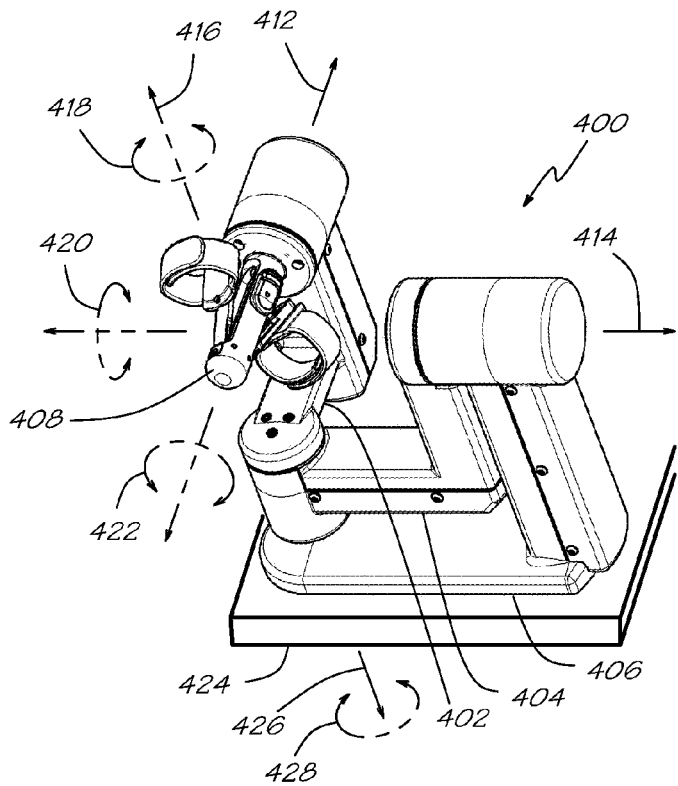
FIG. 4 shows a pictorial representation of an input device that may be used to control a robotic surgical system.

FIG. 4 shows a pictorial representation of an input device 400 that may be used to control a robotic surgical system. An input handle 408 may be grasped by an operator to provide linear and angular position input. The portion of the input device 400 shown allows the input handle 408 to be rotated with three degrees of freedom to provide three angular position inputs. The input handle may be rotated about a first axis 412 of the handle to provide a roll input 422. The handle may be rotatably supported by a first L-shaped link 402. The first L-shaped link 402 may be rotatably supported by a second L-shaped link 404. The handle 408 may cause the first L-shaped link 402 to rotate about a second axis 416 to provide a yaw input 418. The second L-shaped link 404 may be rotatably supported by a third L-shaped link 406. The handle 408 may cause the second L-shaped link 404 to rotate about a third axis 414 to provide a pitch input 420.

The third L-shaped link 406 may be rotatably supported by a base 424. The third L-shaped link 406 may rotate about an axis 426 that provides a fourth rotational movement 428 of the input device 400. It will be appreciated that this fourth rotational movement 428 is a redundant degree of freedom that allows for internal motion of the linkage that couples the handle 408 to the base 424. It will be further appreciated that the base 424 may provide additional input motions such as translation of the input handle 408, for example position input with three degrees of freedom to provide three linear position inputs.

A first load is applied to the first L-shaped link 402 as the distance between the handle 408 and the handle stop position becomes less than the threshold distance. The first load may be applied to the first L-shaped link 402 by a spring. In another embodiment, the first load may be applied to the first L-shaped link 402 by a drive system. The first load may increase as the distance between the handle 408 and a handle stop position decreases. The load may be removed from the handle when the distance between the handle and the handle stop position is greater than the threshold distance. The handle stop position may be a fixed position relative to a link in the linkage or it may be a dynamic position determined from the overall configuration of the linkage.

A drive system may be coupled to the third L-shaped link 406. The drive system applies a second load to the third L-shaped link 406 responsive to the first load applied to the handle. The second load applied to the third L-shaped link 406 creates internal motion of the linkage such that the distance between the handle and the handle stop position is increased.

The second load applied to the third L-shaped link 406 may be controlled to be sufficient to reduce the first load applied to the handle 408 by the handle stop and to overcome the friction in the linkage. In the configuration of the input device 400 shown in the figure, the axis of rotation 416 between the first and second L-shaped links 402, 404 is coincident with the axis of rotation 426 between the third L-shaped link 406 and the base 424. As the handle 408 is rotated to provide various pitch inputs 420, an angle will be created between these two axes. The second load applied to the third L-shaped link 406 may be adjusted according to the angle between the two axes. For example, the second load may be proportional to a cosine of an angle between the two axes.

Figure 5:
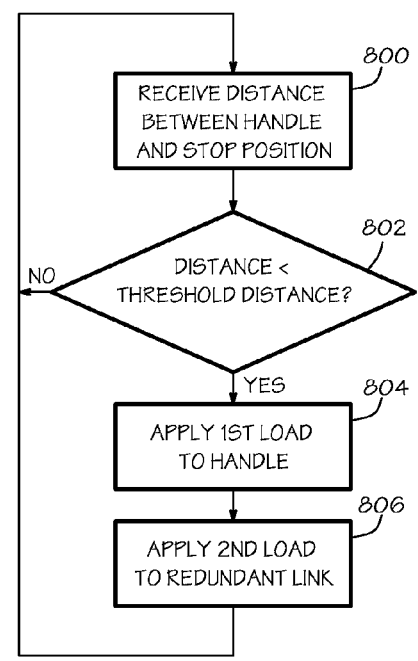
FIG. 5 is a flowchart for a method of controlling a robotic surgical system.

FIG. 5 is a flowchart for a method of controlling a robotic surgical system. A handle is coupled to a base by a linkage. The handle is manually moved relative to the base to provide a position input. A controller receives the distance between the handle and a handle stop position 800. The handle stop position may be a fixed position relative to a link in the linkage or it may be a dynamic position determined from the overall configuration of the linkage. When the distance between the handle and the handle stop position is less than a threshold distance 802, the controller applies a first load is to the handle 804. The first load may increase as the distance between the handle and the handle stop position decreases. A second load is applied to a redundant link 806 of the linkage that couples the handle to the base to create internal motion of the linkage without moving the handle relative to the base such that the distance between the handle and the handle stop position is increased. A sufficient second load is applied to the redundant linkage by the drive system to create internal motion that reduces the first load applied to the handle by increasing the distance between the handle and the handle stop position and to overcome friction in the linkage.

A spring may apply the first load to the handle. In another embodiment, a drive system coupled to the handle may apply the first load to the handle. The handle stop position may be a fixed position relative to a link in the linkage. In another embodiment, the handle stop position may be a dynamic position determined from the overall configuration of the linkage.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

What is claimed is:

1. An input device comprising:
   a base;
   a handle manually movable relative to the base to provide a position input;
   a linkage coupling the handle to the base, the linkage having a plurality of links including a redundant link that permits internal motion of the linkage such that the linkage can move without moving the handle relative to the base;
   a handle stop that applies a first load to the handle to push the handle away from a handle stop position when a distance between the handle and the handle stop position is less than a threshold distance; and
   a linkage drive system coupled to the redundant link, the linkage drive system to apply a second load to the redundant linkage responsive to the first load, the second load creating internal motion of the linkage such that the distance between the handle and the handle stop position is increased.

2. The input device of claim 1, wherein the first load increases as the distance between the handle and the handle stop position decreases.

3. The input device of claim 2, wherein the first load increases as a velocity of the handle toward the handle stop position increases and decreases as the velocity of the handle away from the handle stop position increases.

4. The input device of claim 2, wherein the second load applied to the redundant linkage by the drive system is sufficient to create the internal motion necessary to reduce the first load applied to the handle and to overcome friction in the linkage.

5. The input device of claim 2, wherein the handle moves with respect to a first axis, the redundant link moves with respect to a second axis, and the second load is proportional to a cosine of an angle between the first axis and the second axis.

6. The input device of claim 2, wherein the handle stop includes a spring that applies the first load to the handle.

7. The input device of claim 2, wherein the handle stop includes a handle drive system coupled to the handle that applies the first load to the handle.

8. The input device of claim 7, wherein the handle stop position is determined from a configuration of the linkage.

9. A method of controlling a robotic surgical system, the method comprising:
- receiving a position input from manually moving a handle relative to a base;
- receiving a distance between the handle and a handle stop position; and
- when the distance is less than a threshold distance,
  - applying a first load to the handle to push the handle away from the handle stop position, and
  - applying a second load to a redundant link of a linkage that couples the handle to the base responsive to the first load, the second load creating internal motion of the linkage without moving the handle relative to the base such that the distance between the handle and the handle stop position is increased.

10. The method of claim 9, wherein the first load increases as the distance between the handle and the handle stop position decreases.

11. The method of claim 10, wherein the first load increases as a velocity of the handle toward the handle stop position increases and decreases as the velocity of the handle away from the handle stop position increases.

12. The method of claim 10, wherein the second load applied to the redundant linkage by the drive system is sufficient to create the internal motion necessary to reduce the first load applied to the handle and to overcome friction in the linkage.

13. The method of claim 10, wherein the handle moves with respect to a first axis, the redundant link moves with respect to a second axis, and the second load is proportional to a cosine of an angle between the first axis and the second axis.

14. The method of claim 10, wherein applying the first load to the handle includes providing a spring that applies the first load to the handle.

15. The method of claim 10, wherein applying the first load to the handle includes providing a drive system coupled to the handle that applies the first load to the handle.

16. The method of claim 15, further comprising determining the handle stop position from a configuration of the linkage.

17. An input device comprising:
- means for providing a position input relative to a base;
- means for applying a first load to the means for providing the position input when a distance between the means for providing the position input and a stop position is less than a threshold distance; and
- means for applying a second load to a redundant link of a linkage responsive to the first load, the linkage coupling the means for providing the position input to the base, the redundant link creating internal motion of the linkage without moving the means for providing the position input relative to the base, the second load increasing the distance between the means for providing a position input and the stop position.

18. The input device of claim 17, wherein the first load increases as the distance between the means for providing a position input and the stop position decreases.

19. The input device of claim 18, wherein the first load increases as a velocity of the handle toward the handle stop position increases and decreases as the velocity of the handle away from the handle stop position increases.

20. The input device of claim 18, wherein the second load applied to the redundant linkage by the drive system is sufficient to create the internal motion necessary to reduce the first load applied to the means for providing a position input and to overcome friction in the linkage.

21. The input device of claim 18, wherein the means for providing a position input moves with respect to a first axis, the redundant link moves with respect to a second axis, and the second load is proportional to a cosine of an angle between the first axis and the second axis.

22. The input device of claim 18, wherein the means for applying the first load includes a spring that applies the second load to the means for providing the position input.

23. The input device of claim 18, wherein the means for applying the first load includes a drive system coupled to the means for providing the position input.

24. The input device of claim 23, further comprising means for determining the stop position from a configuration of the linkage.

* * * * *